United States Patent [19]

Moser

[11] Patent Number: 5,117,692

[45] Date of Patent: Jun. 2, 1992

[54] METHOD AND CONFIGURATION FOR MEASURING A TWO-DIMENSIONAL REFLECTIVE STRUCTURE

[75] Inventor: Urs Moser, Zurich, Switzerland

[73] Assignee: Institute of Biomedical Engineering and Medical Informatics of the University of Zurich and the Swiss Federal Institute of Technology Zurich, Zurich, Switzerland

[21] Appl. No.: 499,412

[22] PCT Filed: Oct. 19, 1989

[86] PCT No.: PCT/EP89/01246

§ 371 Date: Jun. 19, 1990

§ 102(e) Date: Jun. 19, 1990

[87] PCT Pub. No.: WO90/04793

PCT Pub. Date: May 3, 1990

[30] Foreign Application Priority Data

Oct. 19, 1988 [CH] Switzerland .................. 3886/88

[51] Int. Cl.$^5$ ............................................. G01N 9/24
[52] U.S. Cl. ............................................. 73/626; 73/602
[58] Field of Search .................. 73/602, 620, 623, 625, 73/626, 627, 628; 128/661.01, 661.07, 661.09, 662.04, 660.01

[56] References Cited

U.S. PATENT DOCUMENTS

| | | | |
|---|---|---|---|
| 4,097,835 | 6/1978 | Green | 73/628 |
| 4,596,145 | 6/1986 | Smith et al. | 73/626 |
| 4,831,601 | 5/1989 | Breimesser et al. | 73/626 |
| 4,835,689 | 5/1989 | O'Donnell | 73/626 |

*Primary Examiner*—Hezron E. Williams
*Assistant Examiner*—Louis M. Arana
*Attorney, Agent, or Firm*—Notaro & Michalos

[57] ABSTRACT

In order to measure a layer in the volume of a reflective structure, a transducer matrix emits at least one sonic or ultrasonic wave packet which coherently impinges on the layer. The echo signals at each element of the transducer matrix are processed separately, on the basis of determined distances between transducer elements and volume elements, and signals corresponding to the echo of each volume element on all the transducer elements of the matrix are calculated by correlation. By emitting two or more wave packets and evaluating the resulting phase or frequency difference therebetween, a two-dimensional velocity field of the structure in the layer can also be determined.

21 Claims, 4 Drawing Sheets

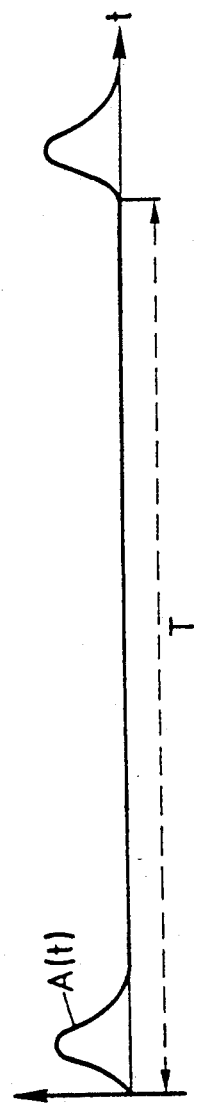
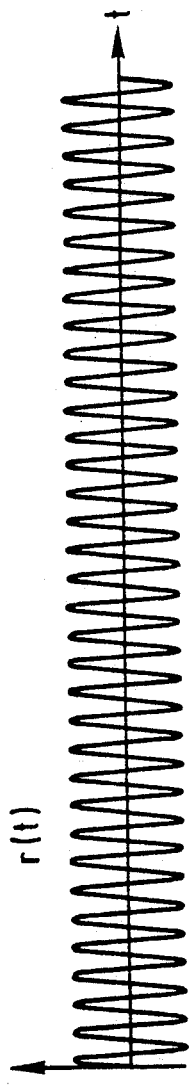
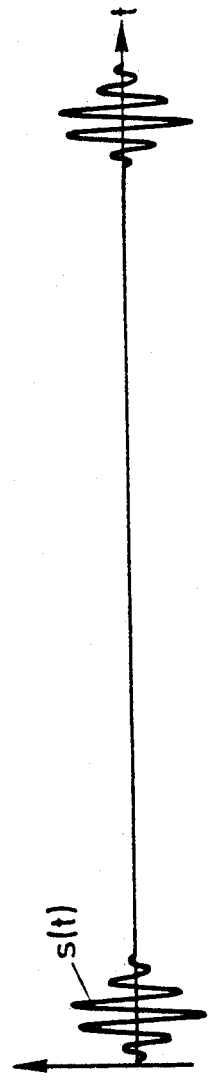
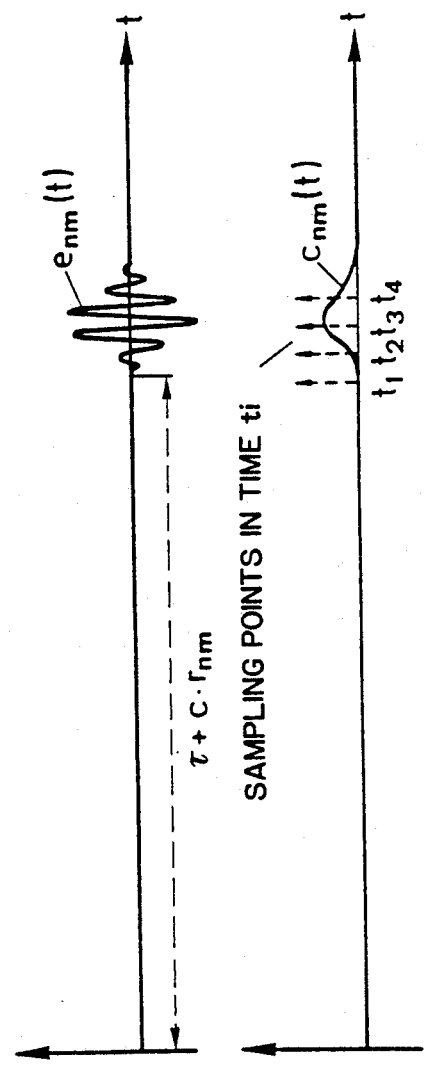
FIG. 4a
FIG. 4b
FIG. 4c
FIG. 4d
FIG. 4e

METHOD AND CONFIGURATION FOR MEASURING A TWO-DIMENSIONAL REFLECTIVE STRUCTURE

FIELD AND BACKGROUND OF THE INVENTION

The present invention relates, in general, to a method and arrangement for measuring a reflective, two-dimensional structure in a layer of a volume by means of evaluating sonic or ultrasonic echoes, and, in particular to a new and useful method and arrangement for measuring a velocity field of such a structure.

In particular in connection with the ultrasonic pulse Doppler technique for measuring fluid velocities in fluid carrying scattering centers, it has been known for more than two decades (Baker, "Pulsed Ultrasonic Blood Flow Sensing", IEEE Trans. SU-17/3, p. 170 (1970)) to determine the velocity of the fluid by evaluating the Doppler frequency of an echo signal originating from a given distance or its phasing with respect to a stable reference signal. Thereby, due to the Doppler effect only the velocity component pointing in the beam-return direction is determined.

Due to the different distances existing at a two-dimensional layer with respect to a receiver, a two-dimensional structure could not be measured in accordance with the above cited technique even when the known method was applied to a stationary structure.

In a further developed called a multi-channel apparatus (McLeod, "A Multiple Gate Pulsed Doppler Flowmeter", Proc. IEEE Ultrasonic Symp. Miami, (1970)), echoes exclusively from different distances were sequentially evaluated and the results were displayed quasi-simultaneously according to a velocity profile along the beam of acoustic irradiation. With this method too, and due to the above cited distance conditions at a two-dimensional layer and to the actually one-dimensional measuring principle, measuring of the type stated above is not possible.

From DE-PS 24 06 630 a method for measuring a velocity profile of a flowing fluid carrying reflective structures based on the evaluation of sonic or ultrasonic echoes became known, by which determination of the velocity profile became possible without actually preselecting the distances. With this method too, it is not possible to measure a two-dimensionally extended layer with respect to reflective structures due to the above stated distance conditions, in the event the approach is applied to stationary structures.

Furthermore it is known to deflect a sonic echo beam differently, by means of so-called phased array sector scanners. The sonic echo beam is deflected in a plane containing the transmitter/target axis by different transmitter stimulation to determine scatter center velocities along the currently selected axis of acoustic irradiation. This is done sequentially and in different directions in the plane. In this way, the two-dimensional velocity field is sampled in this plane and in the "B mode" known to the person skilled in this art.

With this method, so called echography is only possible in a plane which is in the plane with the target axis, even for stationary structure. When using this method for its primary purpose, namely for the measurement of a velocity profile, a further problem is encountered: For a real-time measurement, the measuring time for sampling in the plane must be limited so that either only short measuring time periods are possible in each current beam direction or, when lengthening these time periods, a measurement is only possible in a few sampling directions.

In the case of a so-called Color Doppler Apparatus (Chihiro, "Real-Time Two-Dimensional Blood Flow Imaging Using an Autocorrelation Technique", IEEE Trans. on Sonics and Ultrasonics, Vol. SU 32, No. 3, (1985)), primarily the measuring time in the respective beam directions is strongly limited so that, due to the lack of definition, the Doppler frequency can only be determined very imprecisely.

SUMMARY OF THE INVENTION

An object of the present invention is to create a method and apparatus of the kind initially stated, by means of which, when applied to stationary structures, their structured echo can be detected in real-time, avoiding the above mentioned disadvantages or, when applied to moving structures, their two-dimensional velocity field can be detected in quasi-real-time, avoiding the above stated disadvantages.

Accordingly, an object of the present invention for evaluating acoustic echoes from stationary structures, comprises emitting at least one packet of acoustic signal, providing a two-dimensional arrangement of multiple acoustic sensors, defining a target layer within the object, the layer having a multitude of layer elements which are all at a predetermined distance from each of the sensors, determining from the distances the echo receiving times at which each of the sensors is expected to receive the echo of each of the layer elements, sampling the echo-representing output signal of each sensor at the expected receiving time to produce a multitude of sample signals, each representing a component of the output signal of the sensor which is primarily caused by the echo of one of the layer elements, combining all the sample signals primarily caused by one layer element and sampled at all outputs of the sensors to form a composite single signal which is primarily caused by one layer element on the arrangement of sensors, combining all of the sample signals to form a multitude of composite signals corresponding to a multitude of layer elements and storing the multitude of composite signals as an image of the reflective structures within the target layer of the object.

Another object of the invention is to provide an apparatus for practicing the method.

For an object having a moving structure, the method of the invention includes the step of determining the phase shift between the reflective multitudes of stored composite signals, the phase shifts corresponding to the velocity of the layer elements. An arrangement is also provided for practicing the method of evaluating acoustic echoes from a moving object.

Thus, in principle, be it in the field of echography, i.e., for stationary structures or for velocity measurements, the aforestated disadvantages are eliminated in that simultaneously the entire two-dimensional area of interest is acoustically irradiated and, apart from delay time differences given by the different spatial positions of volume elements in the layer of interest relative to the transmitter and/or receiver, simultaneous evaluation is performed (except with respect to calculating times) on the echoes received from the entire target area of interest.

Although it is quite possible to generate the transmitted wave packet so that it reaches the layer non-coherently and to subsequently consider mathematically this non-coherence (phase unbalance) by consideration of the locally different distances between transmitter and volume elements of the layer, according to the invention, in a preferred embodiment of the invention, the transmitted wave packet is generated so that it reaches the layer at least approximately coherently (at like phase) so the need for considering the stated different in transmit/volume element distances, is omitted.

The transmitted wave packet is preferably generated by stimulating a multitude of acoustic sources according to the invention, so that it becomes possible, by the stimulation which is correct with respect to time and phase in the multiplicity of transmitting sources, to take into consideration possible differences of distances between individual sources and individual volume elements of the layer. By this stimulation (which is correct with respect to time and phase), regardless of the spatial position of the layer of interest with respect to the multiplicity of provided sources, the transmitted wave packet generated by the multiplicity of sources together, as preferably demanded, impinges coherently on the layer of interest.

Simpler conditions exist if the sources are in a planar arrangement.

Although the multiplicity of sensors can also spatially positioned in a three-dimensional configuration and the distance differences occurring according to the spatial sensor configuration and the target layer can be considered mathematically, it is suggested in a preferred embodiment to position the sensors in a planar matrix.

Since, with an essentially planar transmitter configuration as well as also with an essentially planar sensor arrangement, target layers positioned in any manner in space may be measured by mathematical consideration of the corresponding transmitter to volume-element or volume-element to sensor distances, according to another feature of the invention the steps of transmitting and receiving are accomplished from the same configuration. Here a spatial, preferably planar configuration of transmitter and receiving transducers is provided. Consequently there results a constructionally compact electronic unit for stimulation and evaluation.

The transmitted wave packet is, if generated by means of a multiplicity of sources, preferably generated using a stimulation signal from one stable reference signal. Accordingly, the potentially necessary time and phase shifts of the stimulations of the individual sources are defined with respect to the stated reference signal.

Furthermore the reference signal may be used for the demodulation of the echo signals whereby preferably this demodulation is carried out on the electrical side of the sensors, implemented actually as acoustic pressure/electrical transducers.

Moreover according to another aspect of the invention, the echoes, in particular the volume-element echoes of each sensor, are digitized and stored, and this is done preferably after demodulation of the echo signals.

By a further preferred approach according to the invention, it is achieved that echoes originating from the volume-element which impinge on all the sensors are mathematically equalized in phase so that all these echoes originating from one volume element at all sensors can be exploited together.

Fundamentally, by knowing the corresponding echo receiving times or distances at each sensor, echoes originating from all volume-elements are identified at each sensor and are subsequently so mathematically combined that the echoes occurring at all sensors from one volume element of interest are amplified relative to the echoes impinging from other volume elements at the sensors.

This is carried out for all volume elements so that at the end, there results from the entire sensor arrangement one total volume element echo signal for each volume-element.

If, as was explained above, mathematically coherence of the echoes from one volume element at all sensors is achieved, the "signal-to-noise" ratio is improved by mathematical combination using summing, according to the invention.

These sensor-specific echoes wherefrom the volume element echoes are identified, are stored as data for all identification and calculation steps, to obtain the number of total volume element echoes corresponding to the number of volume elements and consequently the layer echo. This can be used to find a volume flow through the target layer.

For the above stated measuring of the two-dimensional velocity field of the structure in the target layer, the process is performed according to the invention, so that at least two transmitted wave packets are generated in the elucidated manner, staggered in time, and their respective echoes are evaluated according to the explanations given up to now. By additional evaluation of the differences of at least two sets of total volume element echoes, the velocity of the structures in the respective volume elements is determined, and, over all the volume elements, lastly the velocity distribution or velocity field of the structure over the layer is obtained.

The advantages accomplished with the method according to the invention, be it directed toward stationary structures, i.e., for echography or, toward moving structures for detecting the velocity field, include the ability to make real-time measurements, where the problem of limited measuring time is eliminated since the entire area of interest which is divided into the stated volume-elements, is simultaneously measured. Through the markedly shortened measuring time it is possible in real-time operation to achieve good local resolution as well as high accuracy, in particular for velocity measurements.

A further advantage of the method according to the invention consists in that, in contrast to the above stated color Doppler method, the sampled target layer does not comprise or must not comprise the main axis of acoustic irradiation but rather can be perpendicular to it at a selectable distance from the sensor configuration. It must be pointed out that by postulating the distances of each sensor from each volume element of the target layer, the two-dimensional measurement becomes independent of the position of the layer with respect to the main axis of acoustic irradiation of the sensor configuration. With the aid of postulating the distances it is in fact determined which target layer is to be measured or how it is selected to lie in space with respect to the transmitter configuration. It is understood therein that by changing such "distance tables" a layer by layer measurement in rapid sequence becomes possible.

According to the invention, the volume flow through the target layer can be determined by summation of the volume element velocities. Reference is made in this connection to Moser, "Inharente Grenzen von Ultraschall-Blutflussmessverfahren" {Inherent limits of ultrasonic blood flow measuring methods}, Dissertation, ETH No. 8567, 1988.

BRIEF DESCRIPTION OF THE DRAWINGS

The invention will now be explained by example in conjunction with the drawings, wherein:

FIG. 4a illustrates the envelope function of transmitted wave packets generated according to the invention, on a time axis;

FIG. 4b illustrates the wave or carrier signal on the time axis;

FIG. 4c illustrates the carrier signal according to FIG. 4b, amplitude modulated with the envelope function for the generation of the transmitted wave packets;

FIG. 4d illustrates a wave packet received at a receiving sensor element from of a volume element of the target layer plotted over time; and FIG. 4e illustrates the envelope signal of the echo wave packet according to FIG. 4d and with respect to the sampling times $t_i$ according to FIG. 2.

DESCRIPTION OF THE PREFERRED EMBODIMENTS

Figure 1:
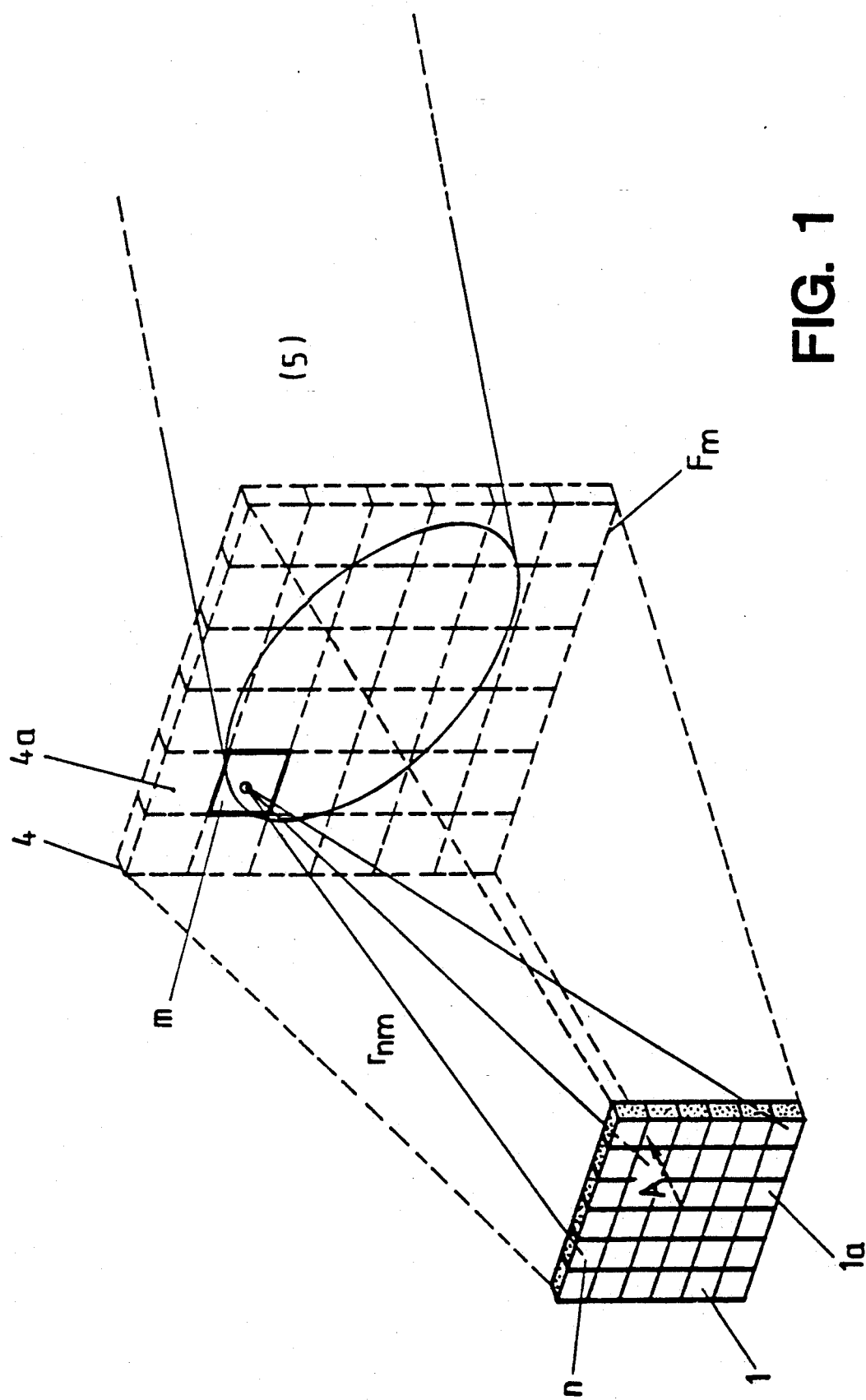
FIG. 1 schematically illustrates the spatial arrangement of a preferred transmitter/receiver configuration in the form of a transducer matrix as well as a layer to be measured, in the special case of a layer positioned parallel to the transducer plane.

FIG. 1 schematically illustrates a preferred arrangement of sources for generating the transmitted wave packet and of sensors for receiving the echoes scattered back. In this preferred embodiment the same elements or transducers 1 are used as the transmitter sources and as the receiver sensors. In the preferred embodiment, the sensor/sources are in matrix-form and are essentially in a plane 1a.

Figure 2:
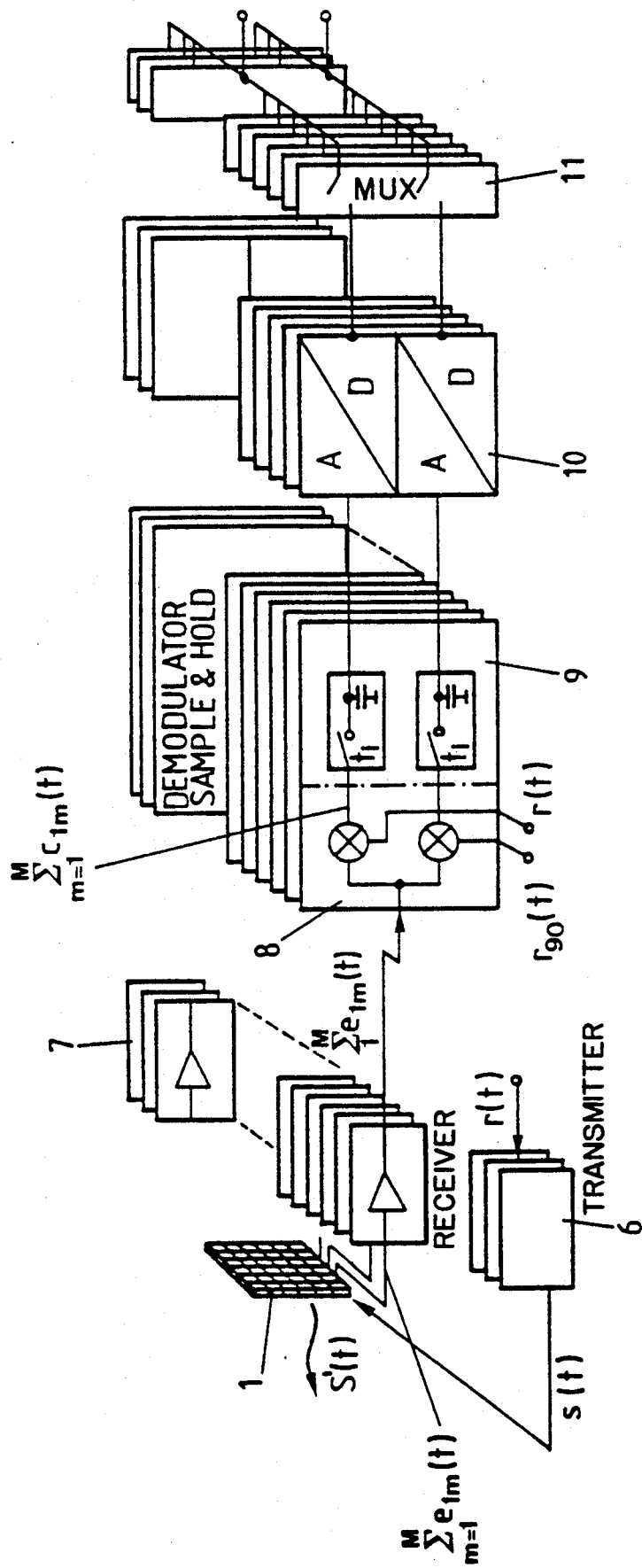
FIG. 2 is a schematic representation of a stimulation unit as well as an echo signal evaluation unit for signal digitization and for multiplexing of the digitized signals.

As is apparent in FIG. 2, the transducer elements 1 are stimulated by means of one or several transmitters 6 for the joint output of a transmitted wave packet s'(t). As can be seen again in FIG. 2, one receiver 7 is connected to each of the transducer elements 1 of FIG. 1. The receiver 7 amplify the echo signals received from the transducer element 1 and convert them into electrical signals.

The output signals of the receivers 7 are, as is customary in multichannel Doppler apparatus (see the "Mc-Leod" reference above), mixed orthogonally into the baseband with the aid of a synchronous demodulator. To this end two orthogonal reference signals r(t) and $r_{90}(t)$ are supplied to the synchronous demodulator 8 whereby the reference signal r(t) is additionally used for stimulating the transducer elements 1 via the transmitters 6.

Figure 3:
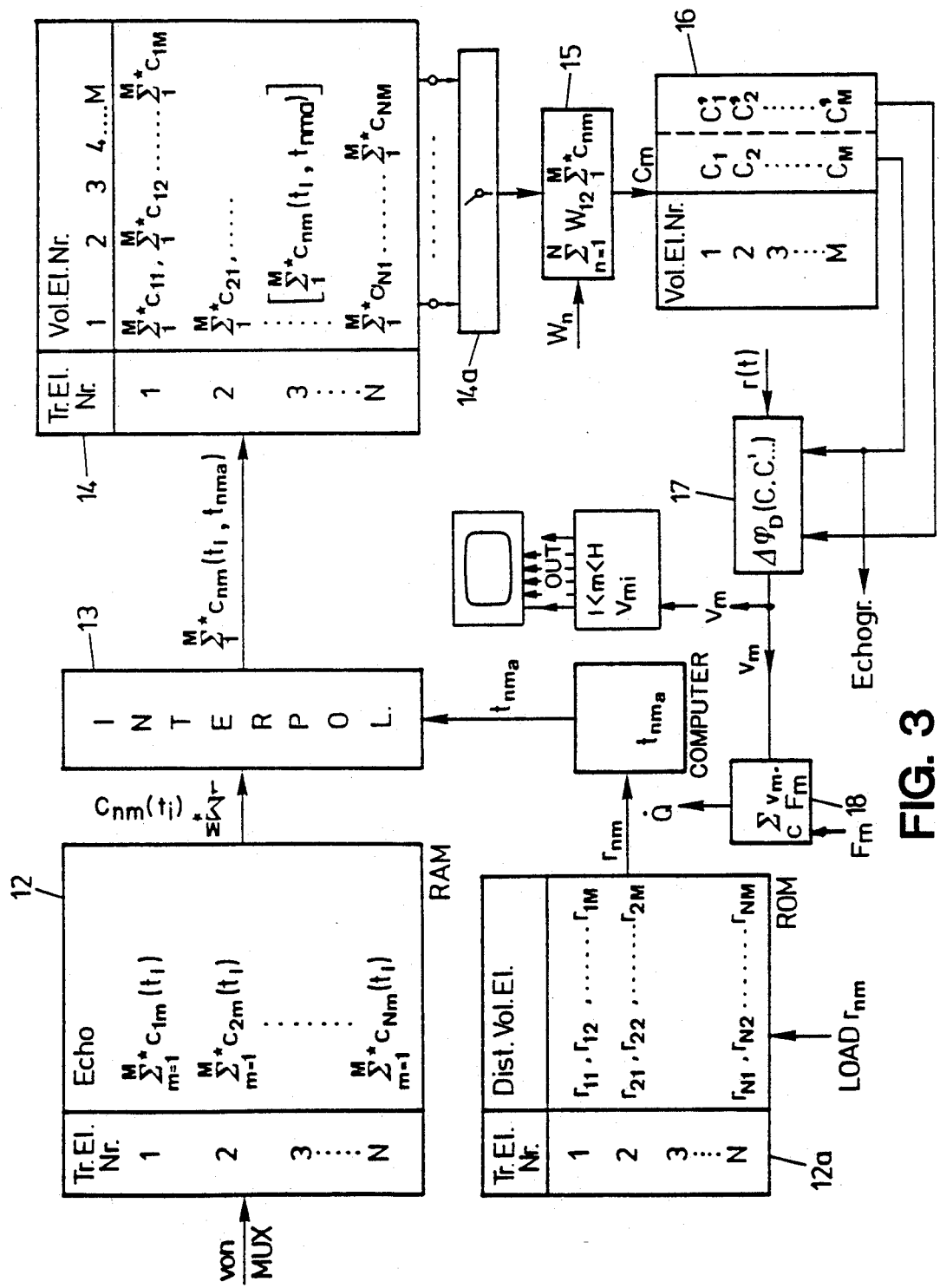
FIG. 3 is a continuation of FIG. 2, showing further processing of the signals on the output side of the multiplexer according to FIG. 2, with reference to a signal flow and function block diagram.

At a few, for example four, predetermined points in time $t_i$ the orthogonal echo signals demodulated at the synchronous demodulator 8 originating from each transducer element 1 are sampled in a sample-and-hold circuit 9 and then supplied to an analog-to-digital converter 10, and are there digitized. The digitized values at the analog-to-digital converters 10 reach, via a multiplexer 11 for intermediate storage, a memory 12 (FIG. 3), preferably a RAM memory.

The transducer elements 1 generate at least one wave packet s'(t) when used for echography, and at least two for velocity field detection. With the carrier frequency $\omega_o$ the transmitted wave packet can be written as follows:

$$s'(t) = A(t)e^{j\omega_o t} \quad (1)$$

where:
A(t): is the envelope of the transmitted wave packet
t: is the time
$\omega_o$: is the carrier angular frequency.

The envelope A(t) of the transmitted wave packet according to FIG. 4a is only briefly different from zero compared with the repetition time T of velocity field measurements. The transmitted wave packet s'(t) can be considered as the product of the envelope A(t) with the quartz-stable reference signal r(t), whereby the reference signal r(t) is shown in FIG. 4b and the resulting transmitted wave packet is shown in FIG. 4c.

The reference signal r(t) can be represented:

$$r(t) = e^{j\omega_o t} \quad (2)$$

The stimulation signal s(t) according to FIG. 2 is transformed by transducer elements 1 into the particular acoustic transmitted wave packets s'(t) which propagate into the acoustic medium where components thereof are reflected by reflective stationary structures contained in the acoustic medium or, if a fluid is the acoustic medium, by moving structures.

According to FIG. 1 the layer area 4 which is to be measured, is subdivided into a number M of volume elements, preferably of equal size whereby in FIG. 1 the special case is represented in which the layer 4 lies in a plane parallel to the transducer plane.

To each of the number of volume elements M, a current number m with $1 < m < M$, is assigned and further the transducer matrix 1a is provided with a total number of N transducer elements 1, numbered with a current number n where $1 < n < N$. At the transducer element No. n the volume element No. m generates the following echo signal:

$$e_{nm}(t) = D\,A(t - \tau - r_{nm}/c)e^{j\omega_o(t-\tau) - jkr_{nm}} \quad (3)$$

with k =
$\omega_o/c$: Wave number
c: sonic speed
D: loss factor
$\tau$ therein signifies the propagation time of the transmitted wave packet from the transducer plane to the layer 4 whereby this propagation time in the special case under consideration is set to be identical for all volume elements. D takes into consideration the attenuation of the sound in the medium as well as scatter losses.

The phase of the received signal at a transducer element No. n from the volume element No. m, i.e. the echo signal $e_{nm}$, reacts very sensitively to changes of the distance $r_{nm}$ which is defined from a considered transducer element 1 to a considered volume element. (In the general case an analogously different $\tau_m$ must be taken into account.) From a considered volume element No. m consequently each transducer element 1 of the matrix 1a receives an echo signal with a different phasing due to the different distances of the volume elements 4a to a considered transducer element 1. The amplitude A(t), in contrast, is a variable which varies relatively little with the distance.

As shown in FIG. 2, at the electrical output of each transducer element 1, for example at that with the No. 1, an echo appears which results from the totality of the echoes $e_{1m}$ generated by each volume element. This echo signal of each transducer element 1 is amplified at receiver 7 and subsequently demodulated at the synchronous demodulator 8.

In the preferred embodiment, as also shown in FIG. 4e, at a few predetermined sampling points in time $t_i$ the orthogonal signals are sampled at the output side of the synchronous demodulator 8 whereby (not shown here) in a customary manner, signal components with the sum frequency $2\omega_0$ are filtered out of the demodulated signal. At the output of the synchronous demodulator appears, with respect to the transducer element No. 1 discussed by example, the sum of all complex volume element echo envelopes, whereby there results from one volume element m, the complex envelope relative to one transducer element n according to:

$$c_{nm}(t) = D\,A(t - \tau - r_{nm}/c)e^{-j\omega_0\tau - jkr_{nm}} \quad (4)$$

This signal contains the full information of the sonic signal. Since the signal is band-limited, for digitization, only a few, for example four, equidistant sampling points at the sampling times $t_i$ suffice as shown in FIG. 4e. The demodulated signals sampled at the stated points in time $t_i$ are, as has been mentioned, converted at the analog-to-digital converters 10 and are supplied in digitized form to the multiplexer unit 11. Via the multiplexer unit 11 they are then loaded into the memory unit 12. In the memory 12 consequently the digitized sums of the complex envelope signals are stored, each assigned to the transducer element No. $n = 1, 2, \ldots N$.

This sum signal must now be structured, i.e., from sampled sums (designed with an asterisk) of the complex envelopes $c_{nm}$, it must be found which echo components originate from which volume-elements.

A memory 12a, for example a ROM, PROM, or EPROM, stores a distance value $r_{nm}$ for each transducer element $n = 1$ to N, to the particular volume elements 4a in the layer 4 according to the FIG. 1.

Actually by defining these distance values it is determined how the layer 4 according to FIG. 1 is to lie with respect to the transducer configuration 1a.

From these different distance values $r_{nm}$ by which in fact volume-element/transducer-element propagation time-specific phase differences $\phi_{nm}$ are defined, "virtual" nominal sampling times $t_{nma}$ are calculated, at which the particular transducer element-specific summed echo signal would need to be sampled at the output of the synchronous demodulator 8 so that, sampled at these predetermined points in time the so sampled signals would correspond to that signal component which oriqinates from a volume element considered on the transducer element 1.

From memory 12, the summed signals of the complex envelope assigned to each transducer element are fed to an interpolator 13 as well as the rated sampling times $t_{nma}$ determined from the distance values $r_{nm}$. In the interpolator the actually required values of the complex envelope sum are determined by numerical interpolation at the actually required volume-element and transducer-element specific sampling times $t_{nma}$.

At the output of the interpolator are the complex envelopes of each volume element m, determined at each transducer element of the No. n under consideration. This includes the phase shift corresponding to the sampling times or interpolation sampling times $t_{nma}$. The values determined at the volume element/sensor-specific sampling times $t_{nma}$ by calculation through interpolation continue to be "noisy" in the sense that these value components still comprise components originating from other volume elements 4a. The signals interpolated according to the $t_{nma}$ sampling times are now loaded into the memory 14. In memory 14, each transducer element is assigned a volume-element, in matrix-like manners. The complex envelope sums interpolated in this way are:

$$c_{nm}^{*} = c_{nm}(t_i)e^{j\omega_0(t_{nma} - t_i)} = c_{nm}(t_i)e^{j\phi nm}, \; i = 1,2,3 \text{ or } 4 \quad (5)$$

Where:

$\phi_{nm}$: is a phase difference depending on the distance $r_{nm}$.

The interpolator 13 carries out this complex multiplication whereby it reads from the table memory 12a the values associated with the particular volume elements and transducer elements.

The sums of the complex envelopes in memory 14 consist of respective sampling values of the total echoes received at each transducer element which were then picked up when, at each transducer element, the echo from a considered volume element arrived, due to the transducer-element to volume-element distance.

When these sampling values (which, as mentioned, are still noisy) are considered for one volume-element and at all transducer-elements, they correspond to echo signals arriving coherently at all transmitter-elements from a respective volume-element, since the distance differences have been accounted for by the specific $t_{nma}$ interpolation times. These values are still infested with noise from non-coherently arriving echo signals of the other volume elements for which the particular $t_{nma}$ points in time are not correct. In the sense of this coherence consequently at all transducer elements the echoes from one respective volume-element are correlated.

All complex sum-envelope values $\Sigma^{*}C_{nm}$ stored and resulting from one respective volume element are summed at a summer unit 15 over all transducer-elements as indicated schematically by a switch-over unit 14a. By suitable choice of weighing factors $W_n$ crosstalk between the individual volume elements can be further suppressed. The stated correlatedness is now emphasized strongly compared to the non-correlatedness. At the output of the summer unit 15 consequently sequentially summed signals $C_m$ occur, i.e. the summed echo signals, summed over all transducer elements 1 from one volume element with the No. m. These summed signals (from summed signals with correlated "summands") result according to:

$$c_m = \sum_{n=1}^{N} W_n \cdot \sum_{1}^{M} c_{nm}^{*}(t_i - t_{nma}) \quad (6)$$

These echo signals, which are now predominantly volume element-specific, are stored in a memory 16.

The complex values $C_m$ contain information about the reflective structures contained in the volume element: Its magnitude is a measurement of reflection, and the phase depends on the relative position of the reflective structures. Consequently the output or the content of the memory 16 already forms the result in the application of the inventive method or of the arrangement for echography, i.e., for non-moving structures.

The technique described up to this point is especially suitable for the measurement of the velocity distribution of the structure. To this end, as already shown in FIG. 4a, at least two transmitted wave packets s'(t) are transmitted and the echoes of both packets, separated by the long time T, are each evaluated as was explained up to now.

Consequently, through the at least two transmitted wave packets and their evaluation from each volume element at least two complex values $C_m$ and $C'_m$ are available in memory 16. For reasons of clarity and in order not to have to explain the entire evaluation method or arrangement twice, only the complex values $C_m$ and $C'_m$ are shown in the memory 16 resulting from two or more wave packets and each assigned to the volume elements.

From the phase shift $\Delta\phi_m$ (C, C'), i.e. the phase shift of the complex values $C_m$ from wave packet echo to wave packet echo, the velocity $v_m$ of the structure in the sense of the Doppler frequency evaluation is determined, i.e. in the direction of the acoustic irradiation.

To this end, in the preferred case with several transmitted wave packets, a temporal sequence of values $C_m$, $C'_m$, $C''_m$ etc. which represent sample values of the Doppler frequencies generated in the mth volume elements is analyzed in known manner. A digital highpass filter (not shown) suppresses the stationary components which for example can be due to vessel walls and are in general superimposed on the Doppler-shifted signal. The filtered signal subsequently reaches the frequency detector 17, which determines the average Dopper frequency and therewith, per volume element, the velocity $v_m$ of the structure.

By summation of the Doppler frequency $f_{Dm}$ determined in this manner for each volume element m the volume flow Q through layer 4 according to FIG. 1 can be determined according to the following formula:

$$\dot{Q} = \frac{c}{2f_0} \sum_{1}^{M} F_m f_{Dm} \quad (7)$$

wherein:

$F_m$: is the area of the volume element projected onto the measuring plane, measuring plane perpendicular to the direction of acoustic irradiation c: is the sonic speed $f_o$: is the frequency of r(t)

$f_{Dm}$: is the Doppler frequency in the mth volume element

The weighing factor $F_m$ takes into consideration the size of the partial areas of the volume elements m.

The volume flow $\dot{Q}$ which in this manner is determined with respect to a layer parallel to the transducer matrix surface, is independent of the direction of the velocity vectors through this layer.

I claim:

1. A method for imaging reflective structures within an object by evaluation of acoustic echoes, comprising the steps of:
   (a) emitting at least one packet of acoustic signal;
   (b) providing a two-dimensional arrangement of a multitude of acoustic sensors;
   (c) defining a target layer within the object, consisting of a defined multitude of layer elements by predetermining the distances between each of said sensors and each of said layer elements;
   (d) determining from said distances expected echo receiving times at which each of said sensors is expected to receive an echo from each of said layer elements, for generating an echo-representing output signal;
   (e) sampling the echo-representing output signal of each sensor at said expected echo receiving times to provide from each sensor, a multitude of sample signals, each sample signal representing a component of the output signal of said sensor which is primarily caused by the echo from one of said layer elements;
   (f) combining all said sample signals primarily caused by one layer element and sampled at all outputs of said sensors to form a composite single signal primarily caused by one layer element on said arrangement of said multitude of acoustic sensors;
   (g) performing said combining for all respective sample signals to form a multitude of composite signals according to said multitude of layer elements; and
   (h) storing said multitude of composite signals as an image of reflective structures within said target layer defined within the object.

2. The method according to claim 1, comprising the steps of repeating steps (a), (e), (f), (g) and (h) and further determining phase shifts between the respective multitudes of composite signals stored, as signals representing a velocity of said reflective structures within said multitude of layer elements.

3. The method according to claim 1, further comprising the step of emitting said packet of acoustic signal and of defining said target layer so that said packet of acoustic signal reaches said target layer at least nearly coherently.

4. The method according to claim 1, further comprising the step of emitting said packet by stimulating a multitude of acoustic sources and thereby controlling relative stimulating time and phasing of said acoustic sources.

5. The method according to claim 4, further comprising the step of stimulating an at least nearly planar arrangement of said sources at least nearly simultaneously.

6. The method according to claim 1, comprising the step of providing said arrangement of said multitude of acoustic sensors in an at least substantially planar matrix.

7. The method according to claim 1, further comprising the step of emitting said at least one packet by means of an arrangement of a multitude of acoustic sources, said multitude of acoustic sources and said multitude of acoustic sensors being both formed by a multitude of transducers each for both emission and reception of acoustic signals.

8. The method according to claim 1, further comprising the step of emitting said at least one packet of acoustic signal by a multitude of acoustic sources and of stimulating said acoustic sources by a respective stimulation signal derived from a stable reference signal.

9. The method according to claim 8, comprising the step of deriving said stimulation signal from a quartz-stable reference signal.

10. The method according to claim 8, further comprising the step of demodulating said echo representing output signal before performing said sampling and demodulating said echo representing output signal by using said reference signal as a demodulation reference.

11. The method according to claim 1, further comprising the step of digitizing said echo representing output signal of each sensor and storing said digitized echo representing output signal before performing said sampling, combining, performing and first mentioned storing steps.

12. The method according to claim 1, further comprising the step of combining all said sampled signals primarily caused by one layer element so that signal components caused by said one layer element are amplified with respect to signal components caused by any other layer elements.

13. The method according to claim 12, further comprising the step of combining said sampled signals primarily caused by one layer element by summing.

14. The method according to claim 2, further comprising the step of summing said signals representing velocities of said reflective structures to form a further signal representative of the volume flow through said target layer.

15. An arrangement for imaging reflective structure within an object, comprising:

emitting means for emitting an acoustic irradiation signal toward the object;

an extended arrangement of a multitude of acoustic sensors;

presettable storage means, containing information data relative to distances between each of said sensors and each of a multitude of predetermined elements forming a target layer to be imagined within the object;

sample means to which a multitude of signals depending each from an output signal of one of said sensors is applied, said sample means being controlled by an output of said presettable storage means so as to sample from all said signals depending each from an output signal of one of said sensors, a sample signal at predetermined times at which said sensors are expected to receive an echo from one layer element, considered and to do so for all layer elements;

correlation means to which said sample signals are applied and which form one signal for each of said layer elements and for all said sensors in common; and storage means at an output of said correlation means to which said signals for each layer element and all said sensors in common are applied, said signals each for one layer element and said sensors in common forming imaging data of said reflective structures within said target layer.

16. The arrangement according to claim 15, said correlation means comprising summation means for summing said sample signals.

17. The arrangement according to claim 15, further comprising analog-to-digital converter means interconnected between said sensors and said sample means.

18. The arrangement according to claim 15, said presettable storage means comprising information data according to said distances, said sample means comprising an interpolator, a time calculator unit being interconnected between said presettable storage means and said interpolator so as to calculate from said distance information data within said presettable storage means, said times, said calculator unit controlling said interpolator to sample said signals depending each from an output signal of one of said sensors at said calculated times.

19. The arrangement according to claim 15, further comprising emission control means controlling said emitter means to output at least two subsequent acoustic irradiation signals separated in time, said storage means comprising storage for at least two sets of said signals each for one layer element and said sensor sin common according to each of said emitted acoustic irradiation signals.

20. The arrangement according to claim 19, further comprising at least one of a frequency and of a phase detector means to which said at least two sets from said storage means are applied, the output signal of said detector means being representative of Doppler frequency caused by said reflective structures within said layer elements and thus of velocity of said structures within said layer elements.

21. The arrangement according to claim 20, comprising further summation means to which the output of said detector means is applied, said further summation means emitting a signal being representative of the flow of reflective structures through said target layer.

* * * * *